United States Patent
Winkelman et al.

(10) Patent No.: US 11,105,795 B2
(45) Date of Patent: Aug. 31, 2021

(54) METHODS AND COMPOSITIONS FOR SIMULATION OF THE DERMAL COMPARTMENT

(71) Applicant: ClearIt, LLC, Marblehead, MA (US)

(72) Inventors: James W. Winkelman, Chestnut Hill, MA (US); Martin E. Schmieg, Marblehead, MA (US)

(73) Assignee: ClearIt, LLC, Marblehead, MA (US)

( * ) Notice: Subject to any disclaimer, the term of this patent is extended or adjusted under 35 U.S.C. 154(b) by 9 days.

(21) Appl. No.: 16/242,683

(22) Filed: Jan. 8, 2019

(65) Prior Publication Data

US 2020/0116704 A1 Apr. 16, 2020

Related U.S. Application Data

(60) Provisional application No. 62/620,313, filed on Jan. 22, 2018.

(51) Int. Cl.
- *G01N 33/50* (2006.01)
- *C12N 5/07* (2010.01)
- *C12N 5/077* (2010.01)

(52) U.S. Cl.
CPC ....... *G01N 33/5044* (2013.01); *C12N 5/0656* (2013.01); *C12N 2503/04* (2013.01); *C12N 2503/06* (2013.01)

(58) Field of Classification Search
None
See application file for complete search history.

(56) References Cited

U.S. PATENT DOCUMENTS

| | | | |
|---|---|---|---|
| 4,877,454 A * | 10/1989 | Charkoudian | C08L 89/00 623/15.12 |
| 6,300,128 B1 | 10/2001 | Morota et al. | |
| 2002/0193875 A1 | 12/2002 | Amano et al. | |
| 2004/0018149 A1 | 1/2004 | Noll et al. | |
| 2005/0129730 A1 * | 6/2005 | Pang | A61L 27/3891 424/423 |
| 2008/0095748 A1 | 4/2008 | Kharazi et al. | |
| 2009/0232878 A1 | 9/2009 | Woodroof et al. | |
| 2010/0255059 A1 | 10/2010 | Marquez et al. | |
| 2014/0024010 A1 | 1/2014 | Akashi et al. | |
| 2014/0271633 A1 | 9/2014 | Hossler | |
| 2015/0351896 A1 * | 12/2015 | D'Lima | A61F 2/02 604/522 |
| 2016/0331439 A1 | 11/2016 | Winkelman et al. | |

FOREIGN PATENT DOCUMENTS

WO 2013191531 A1 12/2013

OTHER PUBLICATIONS

Sigma-Aldrich, "Powdered Media Preparation Instructions" and "Medium 199"; https://www.sigmaaldrich.com/technical-documents/protocols/biology/powdered-media-preparation.html; accessed Nov. 18, 2020 (Year: 2020).*

Doyle, "Generation of 3D collagen gels with controlled diverse architectures", Current Protocols in Cell Biology, vol. 72, p. 10.20.1-10.20.16 (Year: 2016).*

Mohri et al., "Effects of heparin, citrate, and EDTA on plasma biochemistry of sheep: Comparison with serum", Research in Veterinary Science, vol. 86, pp. 111-114 (Year: 2009).*

Maida et al., "Cell Nutrition" in Tissue Engineering, 1st Edition, van Blitterswijk et al., Ed.; Academic Press: London; pp. 327-332 (Year: 2008).*

International Search Report dated May 17, 2019 from corresponding PCT/US2019/012692, pp. 6.

International Written Opinion dated May 17, 2019 from corresponding PCT/US2019/012692, pp. 11.

Gomez et al. "In Vitro and In Vivo Laser Treatments of Tattoos" Arch Dermatol. 2010; 146(1):39-45.

Mitic et al. "What is the difference between heparin, citrate and EDTA tubes for blood collection and what is the effect on DNA?" 2014 (Retrieved: Mar. 7, 2019 (Mar. 7, 2019). https://www.researchgate.net/post/VVhat_is_the_difference_between_heparin_citrate_and_EDTA_tubes_for_blood_collection_and_what_is_the_effect_on_DNA) p. 2-3, Sibtain Afzal.

International Preliminary Report on Patentability, PCT/US2019/012692, dated Aug. 6, 2020, 12 Pages.

* cited by examiner

*Primary Examiner* — Michelle F. Paguio Frising
(74) *Attorney, Agent, or Firm* — Nelson Mullins Riley & Scarborough LLP; Thomas J. Engellenner; Reza Mollaaghababa

(57) ABSTRACT

Methods and compositions for simulating a dermal compartment of skin are disclosed. In one aspect of the invention, methods of producing such a skin model include the steps of admixing a collagenous protein source, a blood protein source, and dermal cells in an aqueous carrier, and then allowing the resulting mixture to solidify to produce a gel. In one technique, at least a portion of the mixture, e.g., the collagenous protein source is first heated and then cooled to induce gelation. For example, the mixture can be heated to at least 50 degrees C. and then cooled to temperature below 5 degrees C. to induce gelation.

23 Claims, No Drawings

METHODS AND COMPOSITIONS FOR SIMULATION OF THE DERMAL COMPARTMENT

RELATED APPLICATIONS

This application claims the priority of U.S. Provisional Application No. 62/620,313, filed Jan. 22, 2018, the disclosures of which are hereby incorporated in their entirety by reference.

TECHNICAL FIELD

The technical field of the invention is skin testing and, in particular, methods and devices for simulation of the dermal compartment.

BACKGROUND

"Skin testing" is a general term that covers the evaluation of the effects of the application of chemical and biological agents, heat, light, radiation of all kinds, intended and unintended natural interventions, medical and cosmetic treatments, drug delivery, and other products and processes applied to the skin. Investigation of new treatments for conditions arising in the skin, or that manifest themselves in the skin, often requires skin testing. Such testing is intended to reveal effects on the skin itself from agents applied to the surface of the skin or introduced after penetration of the outermost layer of skin (the epidermis), into the dermis, or below the dermis and beyond.

Skin testing is also often desirable for evaluating other medical treatment modalities including lasers, ionizing radiation, and thermal (heating or cooling) treatments as well as for studying the effects of cosmetic ingredients or formulations that are applied topically or involve penetration of the epidermis.

Conventional skin testing is often performed, initially, upon small animals such as mice, rats, guinea pigs, rabbits, etc., or large animals such as pigs. Protocols for animal testing must be submitted to and approved by the academic or commercial or other institutions in which they are performed. These protocols can be time consuming to prepare and their approval expensive to obtain and thereafter costly and time consuming to administer. Beyond this there are ethical and humane considerations because the animals can experience discomfort, pain and may even need to be euthanized to complete the studies. Thus, alternatives to live animal testing are desirable for scientific, fiscal and ethical reasons.

Skin testing on human subjects are often the culmination of previous testing on animals. Varying levels of pain and discomfort may accompany such testing. Biopsies and histopathological studies may be required to understand and document the testing outcomes.

Tattoo removal by various modalities is a class of skin treatments that could benefit from better skin testing methods and apparatus. While there are well defined protocols that direct the requirements for trials of medical interventions, and there are some conventional procedural requirements for cosmetic evaluations, there are no generally accepted and agreed upon protocols or requirements for skin testing of tattoo removal procedures.

All skin testing approaches for animal or human subjects suffer from an unavoidable problem caused by the microscopic anatomy of skin. Effects upon the outermost layer of skin, i.e., the epidermis, can be directly visualized by the naked eye or with magnification and can be recorded by photographic means. Reflectance spectrophotometry and fluorescence emission can provide further information about the changes and processes that cause them in the outermost layer of the skin. Direct visualization and imaging of the underlying dermis (the dermal compartment) is not possible due to the overlaying epidermis. Epidermis varies in thickness and the degree of keratinization and it also varies greatly from one part of the body to another. Epidermis can have little, moderate or heavy pigmentation, which typically precludes visualization of the dermis via transillumination. No matter how thin the epidermis, it prevents direct visualization of the dermis to record of changes in the composition, structures or function located in the dermal compartment.

As a consequence of the natural microscopic anatomy of skin, testing for effects below the epidermis of various agents require invasive procedures in animal or human subjects. This invasive interventional activity renders a discontinuity of observable events in any single animal or subject. It also introduces substantial expense to the study. There are, in addition, strong objections to the sacrifice or mutilation of animals for cosmetic experimentation and evaluation.

For these and other reasons, it is desirable to have available methods, compositions and systems to replace or minimize the need for animal or human experiments to predict the effects of interventions upon the dermis. These considerations are applicable to testing of modalities for tattoo removal as well as the testing of cosmetics, cosmetic treatments, medications and the specific treatment of dermatologic disorders that manifest themselves in the dermis, including benign and malignant tumors, vascular malformations, allergic disorders, treatment of foreign bodies that lodge in the skin, functional disorders and other diseases with secondary effects in the skin and virtually any and all pathological conditions that manifest themselves in the skin.

SUMMARY OF THE INVENTION

Methods and compositions for simulating a dermal compartment of skin are disclosed. In one aspect of the invention, methods of producing such a skin model include the steps of admixing a collagenous protein source, a blood protein source, and dermal cells in an aqueous carrier. The resulting mixture is allowed to solidify to produce a gel. In one technique, at least a portion of the mixture, e.g., the collagenous protein source, is first heated and then cooled to induce gelation. For example, a collagen component can be heated to at least 50 degrees C. and then cooled to temperature below 5 degrees C. to induce gelation. Alternatively, gelation can be induced by radiation or any other gelation process.

Collagenous proteins account for about ninety percent of the solid content of the natural dermis. Accordingly, these proteins are desirable component of dermal compartment-simulating compositions. The collagenous protein source can include gelatin, e.g., porcine gelatin, which is heterogeneous mixture of water-soluble, high average molecular mass proteins extracted by boiling pig skin, tendons, ligaments, bones, etc. in water.

The blood protein source can be a non-clotting blood derivative such as blood serum or an anticoagulant-treated blood plasma. The anticoagulant can be ethylene diamine tetraacetic acid (EDTA), heparin or a citrate.

The dermal cells can include cultured human fibroblasts, blood cell derived cells such as the cultured monocyte derived TPH-1 cells, or other naturally occurring or tissue derived cells. The term "dermal cells" used henceforth is meant to include any of these cells or other cells of other type or origin that can assist in simulating dermal cellular content for modeling purposes. In certain embodiments, the dermal cells can be coated with a coating substance, such as collagen and/or other extracellular matrix proteins, to inhibit cellular disintegration, e.g., during mixing or heating of the composition. In certain embodiments, the dermal cells (and optionally other heat-sensitive components) can be added to the mixture after the collagenous protein component has been heated and at least partially cooled, e.g., to room temperature. Such heat sensitive components can be blended into the mixture at any time prior to gelation.

The aqueous carrier can be blood bank saline (an isotonic solution of salt at 0.90% w/v; 0.90% sodium chloride irrigation solution USP that may contain NaOH and/or HCl for pH adjustment to pH of about 5.6 (or more generally from about 4.5 to about 7.0)); phosphate buffered physiologic saline (PBS); PBS with 4% formaldehyde; PBS with cell culture medium; cell culture medium of various compositions. The term "aqueous carrier" used henceforth is meant to include any of these media or other media used in biological experiments.

In another aspect of the invention it has been found that dispersants are useful additives to the compositions to promote dissolution of crystalline and other solid aggregations of collagen proteins. Dispersants can include plasticizers, superplasticizers and surfactants. More generally, dispersants are useful in the mixtures of the present invention to improve separation of particles and/or prevent settling or clumping. In certain embodiments, the dispersant can be include one or more aldehydes, phenols or terpene alcohols, such as those found in essential oils. In certain embodiments, the dispersant can be one or more essential oils, such as cinnamon oil, thyme oil, lavender oil, mint oil, or tea tree oil. In one preferred embodiment, the dispersant is cinnamon oil, or a component thereof, e.g., cinnamaldehyde.

In another aspect of the invention, assay methods are disclosed that can include the step of obtaining a dermal-simulating composition and further include the steps of incorporating a substance, e.g., tattoo ink, into the dermal-simulating composition, administering a test therapy and observing changes in the composition. The substance can be introduced during the admixing step or following gelation.

The step of administering a test therapy can include, for example, administering a cold plasma and/or applying electrical energy. The step of administering a test therapy can further include in some embodiments, applying kinetic motion to a therapeutic test instrument, e.g., by causing a needle-shaped electrode to oscillate or vibrate. Alternatively or additionally, the step of administering a test therapy can include administering a pharmaceutical or chemical test agent, e.g., as part of a screening program to identify potential skin damaging or irritating effects of the test agent.

The step of observing changes in the composition can include visual observation, optical measurement, e.g., with a light meter or colorimeter, or extraction of a portion of the treated composition for physical, chemical or optical measurement. For example, following the administration of a test therapy, a "core" sample can be taken from the composition and analyzed, e.g., optically or microscopically.

In yet another aspect of the invention, compositions are disclosed and claimed for simulating the dermal compartment to test skin treatment modalities. The composition can be formed as a gelled mixture of a collagenous protein source, a blood protein source, and dermal cells and an aqueous carrier. Again, the collagenous protein source of the composition can include gelatin, e.g., porcine gelatin, which is heterogeneous mixture of water-soluble, high average molecular mass proteins extracted by boiling pig skin, tendons, ligaments, bones, etc. in water. The blood protein source used in the composition can be a non-clotting blood derivative such as blood serum or an anticoagulant-treated blood plasma. The anticoagulant can be ethylene diamine tetraacetic acid (EDTA), heparin or a citrate. The dermal cells can include fibroblasts and the aqueous carrier can include distilled water, physiological buffered saline, isotonic saline or mixtures thereof. In certain embodiments, the composition can further include cinnamon oil. In some embodiments, the composition can further include one or more tattoo inks that are incorporated into the mixture pre-gelation or following gelation.

In certain embodiments, the compositions can part of a system having multiple layers. For example, in addition to a main dermal-simulating composition, the system can include one or more additional top layers and/or one or more additional bottom layers. The top and/or bottom layers can be substantially transparent (or more transparent than the main layer) to assist in observing experimental results, e.g., to visualize the progress of tattoo removal.

The one or more top or bottom layers can also serve as a moisture barrier to prevent evaporative losses from the gelled mixture that constitutes the main layer. Alternatively, one or more of the top or bottom layers can serve as a substrate to increase a structural integrity, e.g., to assist in storage, transport or handling, of the composition.

One or more additional layers can also be added to the composition to serve as reservoirs for chemical agents that can impart optical or physical properties to the dermal-simulation compositions. These additional agents can include tattoo inks, cosmetic agents, pharmaceutical agents or reagents to assist in assaying the effectiveness of in vitro tests.

DETAILED DESCRIPTION

The dermis is the tissue compartment that exists immediately below the outer layer of skin, i.e., the epidermis. It varies in thickness and cellular makeup in different parts of the body. It is often quoted as ranging from 2 to 8 mm in thickness. The epidermis itself includes a basilar layer of cells that may lie in a flat layer or with ridges and indentations. Above it is the overlaying stratum corneum with keratin on its outermost surface. The thickness of the layers of squamous cells in the stratum corneum and the amount of keratinization also varies greatly in different locations on the body. The base, or deepest margin of the dermis, sometimes referred to as the subdermis, is above the underlaying fat, muscle and other mesenchymal tissues.

The dermis itself varies in thickness from about 3 mm to 12 mm. There are several structural bodies found in the dermis that are derived from the overlaying epithelium, including hair follicles, sweat glands and sebaceous glands that open to the outside of the body through pores in the epidermis. The normal dermis also contains nerves, small blood vessels and lymphatic channels. The major component of the dermis is collagen and its cell of origin, the fibroblast. Collagen fibers and all the other components of the dermis are surrounded by and suspended in interstitial fluid. This is an aqueous based mixture of many components in dynamic equilibrium with the non-cellular components of blood, i.e., serum, and also with the lymphatic fluid present in the lymphatic channels. Certain cells found in the blood migrate through the walls of capillaries under various circumstance and are found scattered or focally grouped in the dermis. The interstitial fluid is composed of a solution of the salts that are present in serum, dissolved gases and the many other biologic, organic and inorganic molecules essential for the continuing life functions that occur in the epidermal, dermal and subdermal tissues. The overall composition of the dermis has the quality of a semisolid, permeable gel that can have varying degrees of turgidity both naturally and in pathological states.

Full descriptions of the microscopic anatomy and composition of skin, including the dermis, are available in standard textbooks of anatomy, histology, pathology and dermatology. Diseases and physiological disorders that occur in the dermis range from the normal aging process to general or specific inflammatory conditions, to benign and malignant growths arising from cells normally present in the dermal compartment to metastases from distant tissues of origin of other primary malignancies. All these conditions are described in standard medical texts and do not need further detailing in this presentation.

The tattooing process is well described in many literature sources. The mature tattoo has all of the ink particles that were not expressed or exuded out of the skin in the first weeks after tattooing or that had migrated through the lymphatic channels to lymph nodes and elsewhere in the body present in the dermal compartment. Less well described is the distribution of the ink in and among the various constituents of the dermis and the disposition of tattoo inks over time. A review of many sources dealing with this subject reveal that there is not perfect agreement on this very complicated subject. A consensus view is as follows.

Tattoo ink is carried through the epidermis by a single solid needle or gangs of such needles that punch through it into the dermis. Much of the ink exudes through those puncture holes immediately and continues to do so for approximately 1 to 5 days. Acute inflammatory reactions including swelling due to exudation into the dermis of blood plasma from capillaries, accompanied by white blood cells, occurs very rapidly and gradually subsides over 2-3 weeks.

Tattoo inks are generally completely chemically inert and do not directly injure the tissues they contact. However, the ink itself cannot be eliminated from the body by the ordinary biological repair and removal mechanisms that customarily respond to the presence of foreign bodies. This description omits complications of tattooing attributable to the carrier matrix of the ink which can elicit an inflammatory reaction. It also omits complications due to the introduction of infectious organisms or toxic substances. These have been extensively documented to produce acute pustular inflammatory reactions and persistent granulomatous reactions.

Tattoo inks in the dermis initially elicit what is known as a "foreign body reaction". Teleologically, this is the defensive process with which the body responds to materials, or substances, or organisms that are not ordinarily present and part of its own natural state. Common examples of such materials are splinters, chitin from insects, soil, shrapnel and infectious organisms. In the ordinary course of events the presence of tattoo inks in the dermis cause inflammatory swelling, as described above. The particular feature of tattooing is that the remaining ink, that persist after the acute inflammatory reaction, elicits the transformation of a specific type of white blood cell, the monocyte, that has entered the dermis from the capillary circulation, to transform into a tissue macrophage. Tissue macrophages can also develop from precursor cells resident in the dermis.

Macrophages increase in size compared to their precursors and engulf foreign bodies, in this case, the tattoo ink aggregates or particles. They also possess strong digestive enzymes that degrade and digest foreign body materials. But tattoo ink particles, unlike the organic structures such as microorganisms, chitin and even wood splinters, cannot be digested because they are chemically inert. Thus, over time, the great majority of tattoo inks come to be found, trapped indefinitely, in these macrophages. They tend to descend into the deeper portion of the dermis. The macrophage regenerates itself over time or is replaced by a newly formed macrophage and the tattoo ink particle remain engulfed in macrophages indefinitely during the life time of the tattooed person. Approximately 75-80% of the tattoo ink in a mature tattoo are in such macrophages. Other ink particles are present along or under the surface membrane of fibroblasts and the collagen fibers they produce. A lesser amount is present in and around small blood vessels and their outermost cells, the pericytes. In this state a tattoo remains more or less unchanged throughout the life of the host animal or human subject.

The dermal compartment contains so many constituents that it cannot be totally reproduced in-vitro. Further, there is no single composition that can simulate the dermis in all of its many states. Therefore, the basic model described herein is intended to be readily modifiable to most suitably match the conditions found in the object of any particular scientific study. The major constituents of the dermis that need to be present in any variation of a model system include: 1) a collagenous protein source, such as collagen itself or polymerized gelatin as a surrogate; 2) salts in aqueous solution at least including sodium and chloride that approximate their concentration in physiological states and at a pH that occur in the interstitial fluid; 3) plasma proteins at a concentration found in the interstitial fluid; 4) cells of any type representative or consistent with the process being investigated; 5) other materials particular to the process being studied, e.g., tattoo inks.

The compositions of the present invention are stable at ambient temperature and are storable for at least 2 weeks at refrigerator temperature. The compositions also exhibit viscosities within the customary parameters for gels that can resist deformation until sufficient tensile or shear stress is imposed on the surface to penetrate the surface. The compositions also exhibit sufficient optical clarity to serve as skin testing devices. Ideally (in the absence of colored components) the compositions of the present invention exhibit essentially complete transparency through a depth of 2 cm. In the presence of organic or inorganic components that can include particles or other light refracting or opaque elements, the compositions exhibit sufficient transparency to allow direct visualization of changes brought about by external forces. Visualization can be either by eye or other means such as a recording videomicroscope.

EXAMPLES

Suitable gels for the in-vitro model can have many different compositions and properties. The conditions of preparation can also be varied along continuous parameters, within certain limits, and the resulting gels being useable and particularly suitable for particular purposes. Therefore, the specific description below is only one such example. It is well suited for the study of techniques and methods for the removal of tattoos.

Distilled water, isotonic blood bank saline (0.90% w/v), human serum (or EDTA plasma with all biohazard testing completed in a licensed blood donor facility), cinnamon extract (natural cinnamon bark oil in 67% Alcohol and water), fibroblast cells or monocyte (or other) human cells, alive or fixed in 4% formaldehyde in culture medium, and gelatin (Porcine Skin for Ballistic Analysis Type 2. Honeywell/Fluka Sigma Aldrich Co) and tattoo ink (Intenz Products, Inc.) are mixed together. An exemplary preparation includes the following: 1.30 g gelatin, 6 drops of cinnamon oil, 60 mL saline, 20 mL serum, $5 \times 10^6$ cells, and 1-10 drops of undiluted tattoo ink.

The mixture is deposited into Petri dishes (e.g., 6 cm diameter dishes) and heated to at least 50 degrees C., preferably to about 75-78 degrees C. Gelatin (e.g., about 1.30 gm) is added while slowly stirring until it is completely dissolved. The composition is allowed to stand for 30 minutes at ambient temperature before serum is added by stirring into the mix before gelation has occurred. The preparation is transferred to a 4-8 degrees C. refrigerator with a glass cover in place. Gelation is achieved after about 3 hours. The gel should be useable for research purposes for at least 2 weeks. Suitability of the gel can be confirmed by determining that its viscosity and surface tension is the same as it was after initial gelation. The gels typically have a surface tension that withstands penetration by a 1.0 cm diameter based steel rod weighing 35 gm placed in the center of a 1.0 cm deep gel in a 9.0 cm diameter Petri dish.

The invention claimed is:

1. A method for simulating the composition of a dermal compartment, comprising admixing a collagenous protein source, an anticoagulant-treated blood plasma, and dermal cells in an aqueous carrier, and allowing the resulting mixture to solidify to produce a gel, wherein said gel is transparent through a depth of 2 cm.

2. The method of claim 1 wherein at least a portion of the mixture is first heated and then cooled to induce gelation.

3. The method of claim 2 wherein said portion comprises the collagenous protein source and is heated to at least 50 degrees C. and then cooled to a temperature below about 8 degrees C.

4. The method of claim 3, wherein said heated collagenous protein source is cooled to a temperature below about 5 degrees ° C.

5. The method of claim 1 wherein the collagenous protein source comprises gelatin.

6. The method of claim 1 wherein the collagenous protein source comprises porcine gelatin.

7. The method of claim 1 wherein the anticoagulant-treated blood plasma comprises any of EDTA-treated, heparin-treated, or citrate-treated, blood plasma.

8. The method of claim 1 wherein the dermal cells comprises at least one of fibroblasts, and monocytes.

9. The method of claim 1 wherein the aqueous carrier comprises distilled water.

10. The method of claim 1 wherein the aqueous carrier comprises an isotonic saline solution; or phosphate buffered physiologic saline (PBS); or PBS with 4% formaldehyde; or PBS with cell culture medium; or cell culture medium.

11. The method of claim 1 wherein the mixture further comprises a dispersant.

12. The method of claim 11, wherein said dispersant comprises an essential oil.

13. The method of claim 12, wherein said essential oil comprises a cinnamon oil or a component thereof.

14. The method of claim 13, wherein said cinnamon oil comprises cinnamaldehyde.

15. The method of claim 1, wherein the method further comprises storing the gel for up to two weeks at refrigerator temperature following gelation.

16. The method of claim 1, wherein the method further comprises
administering a test therapy to the composition; and
observing changes in the composition.

17. The method of claim 16 wherein the method further comprises incorporating a substance into the dermal-simulation composition.

18. The method of claim 17 wherein the substance comprises tattoo ink.

19. The method of claim 16 wherein the step of administering a test therapy further comprises administering at least one of cold plasma, electric energy and electro-kinetic energy.

20. The method of claim 16 wherein the step of observing changes further comprises at least one of physical, chemical, and optical measurement, and visual observation.

21. The method of claim 20 further comprises at one of transparency, transmittal, reflectivity and colorimetric measurement.

22. The method of claim 16 wherein the step of observing changes further comprises extracting a portion of the composition for analysis.

23. The method of claim 22 wherein the extracted portion is a central part of the sample.

* * * * *